United States Patent [19]
Jankowski et al.

[11] Patent Number: 4,744,790
[45] Date of Patent: May 17, 1988

[54] FAST ACTION CARTRIDGE SYRINGE HOLDER

[75] Inventors: George Jankowski, Media; Michael G. Maietta, Cogan Station; William E. Waters, Malvern, all of Pa.

[73] Assignee: The West Company, Phoenixville, Pa.

[21] Appl. No.: 898,048

[22] Filed: Aug. 19, 1986

[51] Int. Cl.$^4$ .................................... A61M 5/245
[52] U.S. Cl. .................................... 604/232; 604/241
[58] Field of Search ............ 604/232, 240, 241, 234, 604/228, 229

[56] References Cited

U.S. PATENT DOCUMENTS

| | | | |
|---|---|---|---|
| 2,423,762 | 7/1947 | Everett | 604/241 |
| 3,084,688 | 4/1963 | McConnaughey | 604/232 |
| 3,294,089 | 12/1966 | Brookfield | 604/241 |
| 3,372,697 | 3/1968 | Keller | 604/241 |
| 4,585,445 | 4/1986 | Hadtke | 604/234 |
| 4,642,103 | 2/1987 | Gettig | 604/234 |

Primary Examiner—John D. Yasko
Attorney, Agent, or Firm—Eugene E. Renz, Jr.

[57] ABSTRACT

A holder for cartridges or containers for medicaments in injectable form comprising an elongated housing having a pocket for the cartridge, a head assembly including an elongated plunger rod adapted to be attached to the cartridge plunger for actuating the same to effect discharge of medicament from the cartridge and means operatively connecting the head assembly to one end of the housing for actuating a shank portion of the head assembly axially (longitudinally) in the housing. The head assembly and housing is made of dissimilar materials to facilitate relative rotation of the head assembly and housing and resist slippage when the shank exerts an axial force on the cartridge to seat it in the housing.

14 Claims 7 Drawing Sheets

FAST ACTION CARTRIDGE SYRINGE HOLDER

FIELD OF THE INVENTION

The present invention relates to hypodermic syringe devices and more specifically to a reuseable syringe holder for use with disposable cartridges for medicaments in injectable form.

BACKGROUND OF THE INVENTION

Cartridge holders for dispensing parenteral pharmaceuticals by injection are not new per se. For example, the patents listed below show various forms of cartridge holders which are typical of prior art assemblies.

| Inventor | Patent No. | Issue Date |
| --- | --- | --- |
| Kasmauskas | 1,546,491 | July 21, 1925 |
| Cook | Re. 16,836 | Dec. 27, 1927 |
| Brown | 1,704,678 | March 5, 1929 |
| Smith | 1,770,633 | July 15, 1930 |
| Nevin | 1,819,258 | Aug. 18, 1931 |
| Debaz | 2,829,643 | April 8, 1958 |
| Stroop | 2,859,750 | Nov. 11, 1958 |
| Stroop | 2,859,751 | Nov. 11, 1958 |
| Sarnoff | 2,956,563 | Oct. 18, 1960 |
| Sarnoff | 3,115,135 | Dec. 24, 1963 |
| Knight | 3,556,099 | Jan. 19, 1971 |
| Baldwin | 3,848,593 | Nov. 19, 1974 |

Considering in some detail several of the above, Cook U.S. Pat. No. Re. 16,836 discloses a hypodermic syringe which locks a container or ampule 25 in barrel 10 by means of locking slots 19 in cap 17 engaging pins 18. This locking action is said to be the means by which the inner end of the needle punctures closure 26. (Page 1, lines 94 to 101)

Kasmauskas U.S. Pat. No. 1,546,491 shows a hypodermic syringe wherein a capsule 29 is locked between two shells 10 and 14. The relative movement of the shells to each other is both transverse and axial. Axial movement results by means of pin 17 cooperating with cam slot 18. The outer shell 14 is securely attached to the needle 28 while inner shell 10 is securely attached to head 13. Thus, as one shell is rotated with respect to the other, stopper 30 is punctured by the needle. (Page 1, lines 100 to 105)

Brown U.S. Pat. No. 1,704,678 discloses a hypodermic syringe wherein a glass cartridge tube 1 is locked in a tubular-like instrument body 7 by a screw cap 11. The finger supports appear to form a part of screw cap 11. Stopper 3 is pierced by pushing the cartridge onto the needle. The cartridge is pushed by an inwardly protruding portion bearing on the rear of the cartridge, which protruding portion is attached or a part of the screw cap 11 (Page 1, lines 91 to 104).

Debaz U.S. Pat. No. 2,829,643 is of interest in that the finger supports 11 are used as a clamping lever. Pivoting of the finger supports moves tensioning members 6 in an axial direction.

Knight U.S. Pat. No. 3,556,099, discloses a hypodermic syringe assembly wherein a cartridge is locked between two guide members 31 by plug 13. Plug 13 includes ridge portions 36. The plug is axially inserted in the syringe by passing ridges 36 in slots 29 until ridges 36 reach circumferential recesses 37, whereupon plug 13 is turned, moving ridges 36 into recesses 37. This axial movement of plug 13 acts to press on the cartridge, such that diaphragm 17 is pierced by needle 12. (Col. 4, lines 29-33) Alignment of finger grips 39 with grips 39' ensures that plug 13 is locked in place.

The various designs discussed above are of rather complicated construction and have certain functional disadvantages and drawbacks.

None of the patents disclose or suggest a holder providing ease of movement of the parts during assembly and disassembly of a spent cartridge and one providing excellent retaining forces when an axial load is present without the need for separate or retaining clamping members or the like.

SUMMARY OF THE INVENTION

These functional advantages are achieved in the holder of the present invention which is characterized by a novel arrangement of comparatively few parts so that the assembly is relatively economical to manufacture. Thus, the holder essentially comprises a head assembly and housing and novel means in the form of a multiple start screw mechanism for movably mounting the head assembly to the housing so that the parts are actuatable between an "open" position for insertion of a cartridge in the holder and a "closed" position firmly seating the cartridge in a position for administering the injectable product.

The advantages of this design over other previous disclosures is that it prevents a phenomenon known as "overhauling". Overhauling occurs when there is relative motion between the male and the female parts of the screw mechanism whereby the screw disengages or "falls through". Furthermore, the development of the optimum threading mechanism to prevent overhaul includes a specific matching of materials for the interengaging parts. These materials should have physical characteristics such that the frictional characteristics between the two interengaging parts are such that they provide ease of relative motion when there is no axial load applied and provide excellent retaining forces when an axial load is present. These characteristics include differences of hardness between the two materials, such difference being at least 5 on the Rockwell R Scale, and differences of coefficient of friction of at least 0.3. However, the function of this design is not restricted to those materials alone.

The plunger rod is a thermally formed injection molded tubular device commonly known in the medical field. The cartridge housing consists of a high clarity high impact resistant material capable of retaining the glass cartridges under any and all extraneous force applications in a secured and locked manner. The housing is clear such that the cartridge is clearly visible in any position and depth of engagement of the threaded "T" handle of the head assembly.

The "T" handle has two integral stops to prevent disassembly of the syringe holder while in use. The "T" handle is appropriately engaged to provide the maximum occurrence of cartridge visibility through the assembly port of the syringe cartridge body to enhance visibility.

The overall assembly of the housing with the "T" handle provides the required range to capture the open and closed cartridge systems currently known to the medical field. In the open system, the screw captures the cartridge assembly and in the closed systems, the holder first effects puncturing of a distal diaphragm by the proximal side of a double-ended needle assembly, then the screw captures the cartridge assembly.

The head assembly is of a predetermined novel configuration and arrangement to accommodate cartridges of varying lengths and, thus, the holder may be termed "universal".

BRIEF DESCRIPTION OF THE DRAWINGS

These and other objects of the present invention and the various features and details of the operation and construction thereof are hereinafter more fully set forth with reference to the accompanying drawings, wherein.

DESCRIPTION OF THE PREFERRED EMBODIMENTS

Referring now to the drawings and particularly to FIGS. 1–12 thereof, there is illustrated one embodiment of fast action cartridge holder in accordance with the present invention which is generally designated by the numeral 10. The holder 10 is adapted for use with cartridges C of various types and sizes for dispensing parenteral pharmaceuticals by injection. These cartridges typically comprise an elongated hollow tubular body portion 12 typically made of glass having a hypodermic needle 1a mounted at the discharge end of the body portion 14 and a plunger 16 made of an elastomeric material fitted in the open outer end of the cartridge body. The plunger 16 mounts a threaded stud 18 for engagement by a plunger rod 20 of the holder assembly for actuating the plunger 16 axially toward the needle end to discharge the contents of the syringe when desired.

Considering now the holder assembly 10 and specifically the embodiment illustrated in FIGS. 1–12, the holder comprises an elongated housing 21 of generally U-shaped cross section defining an open slot 22 extending the length of the housing. The slot 22 facilitates insertion and removal of the cartridge in the housing in the manner described in more detail below. The lower end of the housing has an end wall 24 having an opening 26 through which the needle and lower end of the cartridge engage. The opening 26, as illustrated, is elongated and somewhat oval shaped and has a beveled, arcuate ramp portion 28 adjacent the closed end of the housing to serve as guide means when initially positioning the cartridge. The inner end of the housing 21 as illustrated has a circumferentially extending internally threaded collar 30 for mounting therein the fast action holder head assembly 32.

Figures 1, 1A, 2:
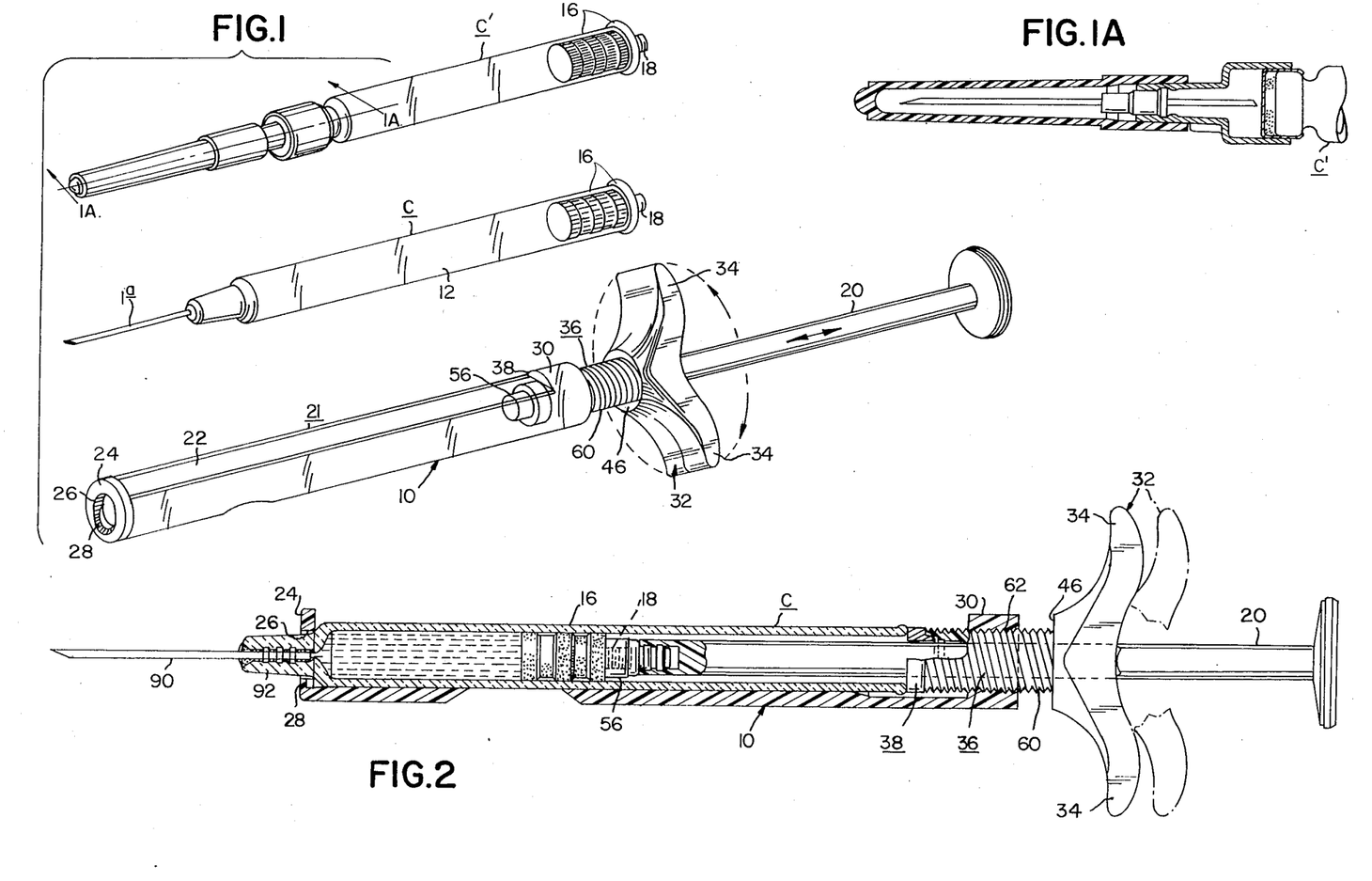
FIG. 1 is a perspective view of a cartridge syringe holder constructed in accordance with the present invention and two cartridge assemblies useable in present invention.
FIG. 1a is an enlarged fragmentary sectional view, taken on the line 1A, 1A of FIG. 1, showing details of a typical double ended needle, closed end cartridge assembly.
FIG. 2 is an enlarged sectional side elevational view of the cartridge syringe holder of this invention showing an open cartridge system mounted in an operative position therein.
Figure 3:
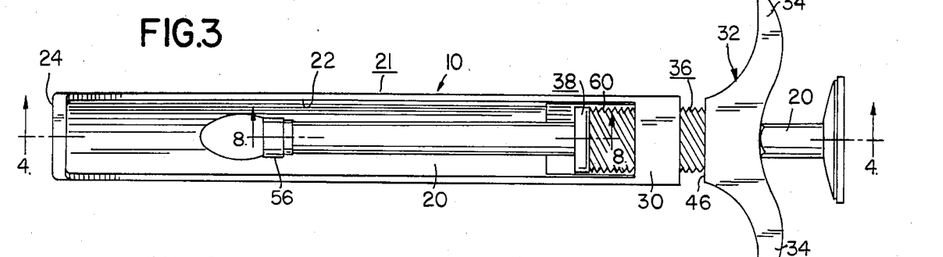
FIG. 3 is a plan view of the cartridge syringe holder shown in FIG. 1.
Figure 4:
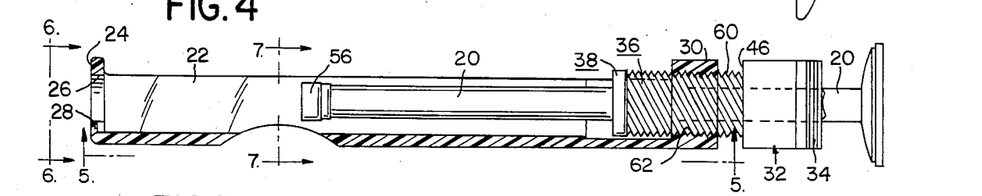
FIG. 4 is a sectional side elevational view taken on the Line 4, 4 of FIG. 3 showing details of construction.
Figure 5:
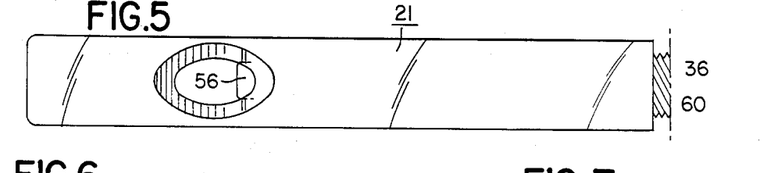
FIG. 5 is a fragmentary bottom plan view taken on the line 5, 5 of FIG. 4.
Figure 6:
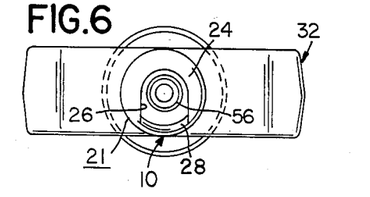
FIG. 6 is an end elevational view taken on the line 6, 6 of FIG. 4.
Figure 7:
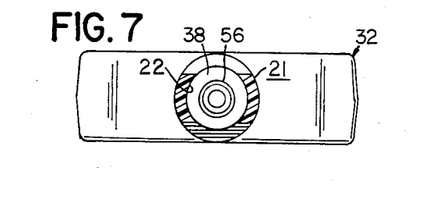
FIG. 7 is a transverse sectional view taken on the line 7, 7 of FIG. 4.
Figure 8:
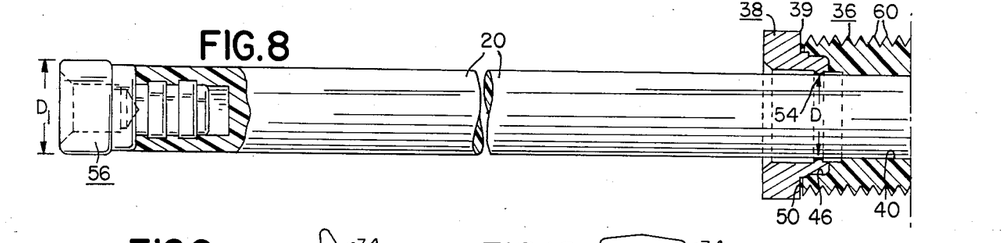
FIG. 8 is a greatly enlarged fragmentary side elevational view, with portions broken away and in section, taken on the line 8, 8 of FIG. 3, showing details of construction of the push rod and its associated stop ring and push rod tip.

The head assembly 32 is mounted at the inner end of the housing 20 for axial movement relative to the collar 30. The head assembly 33 as best illustrated in FIGS. 3 and 6, is T-shaped in cross section having a pair of transversely extending wings 34, 34 with contoured inner surfaces engageable by the fingers of the use during use of the assembly to discharge the contents of the cartridge C. The head includes an elongated, externally threaded shank portion 36 having a stop ring 38 mounted in its outer end. The head assembly has an axially extending bore 40 for mounting an elongated plunger rod 42 therein. The stop ring 38 as illustrated has a shoulder 39 defining an abutment or inner limit position. As illustrated in FIG. 3, at the opposite end, the inner end of the housing 21 abuts the shoulder 46 between the head 32 and the shank 36.

Figure 9:
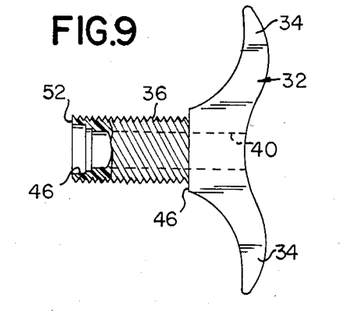
FIG. 9 is a plan view of the head assembly with a portion broken away and in section showing certain details of construction.
Figure 10:
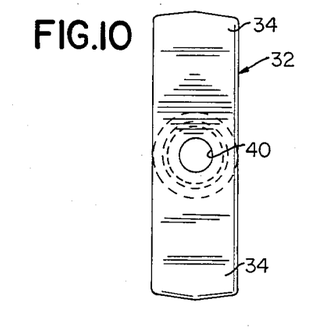
FIG. 10 is a right hand end view of FIG. 9.
Figures 11, 14:
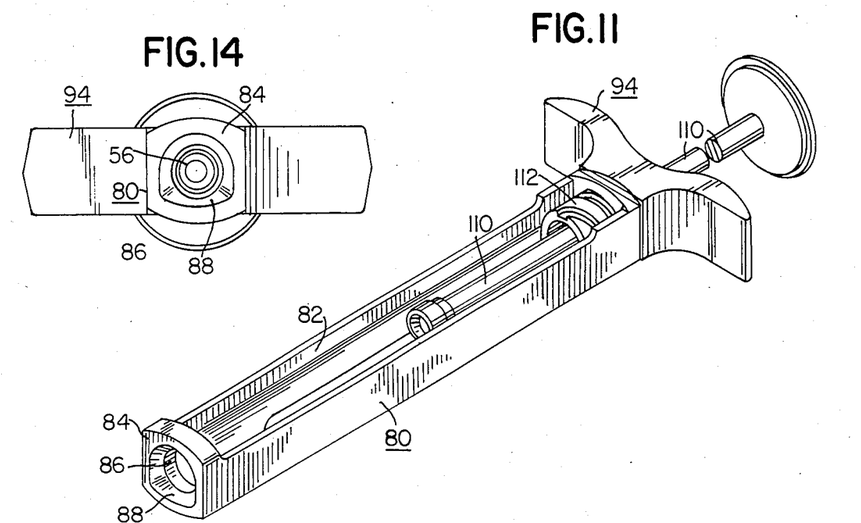
FIG. 11 is a perspective view of another embodiment of the cartridge holder in accordance with the present invention.
FIG. 14 is an enlarged end view taken on the line 14, 14 of FIG. 13.
Figure 12:
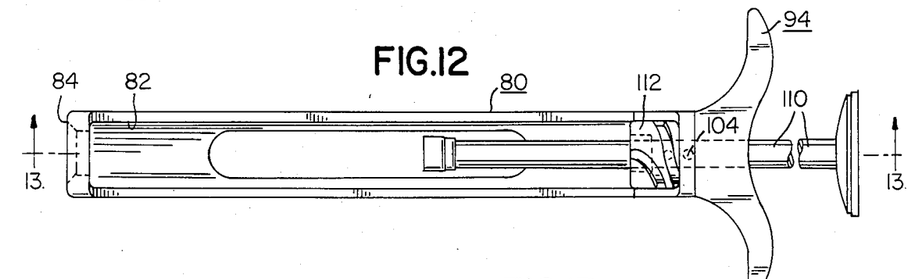
FIG. 12 is a plan view of the cartridge holder shown in FIG. 11.
Figure 13:
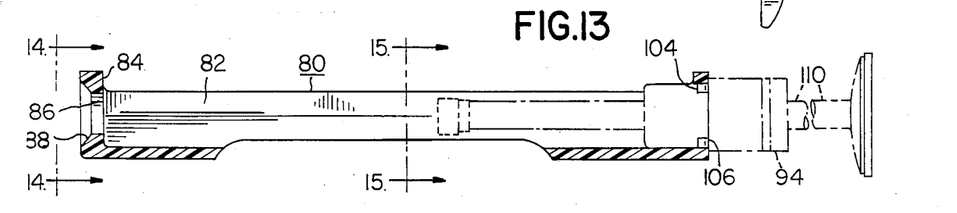
FIG. 13 is a sectional side elevational view taken on the line 13, 13 of FIG. 12 showing details of construction and with the push rod and head assembly removed but shown in phantom outline.
Figure 15:
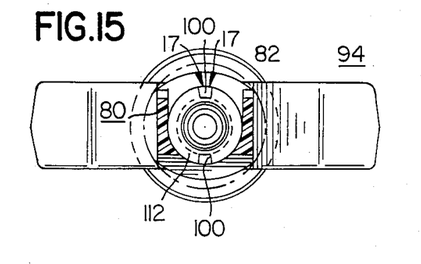
FIG. 15 is an enlarged transverse sectional view taken on the line 15, 15 of FIG. 13.
Figure 16:
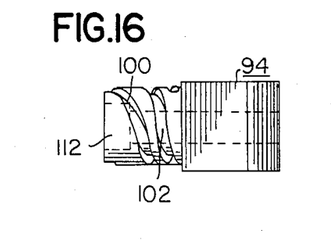
FIG. 16 is a side elevational view of the modified head assembly.
Figure 17:
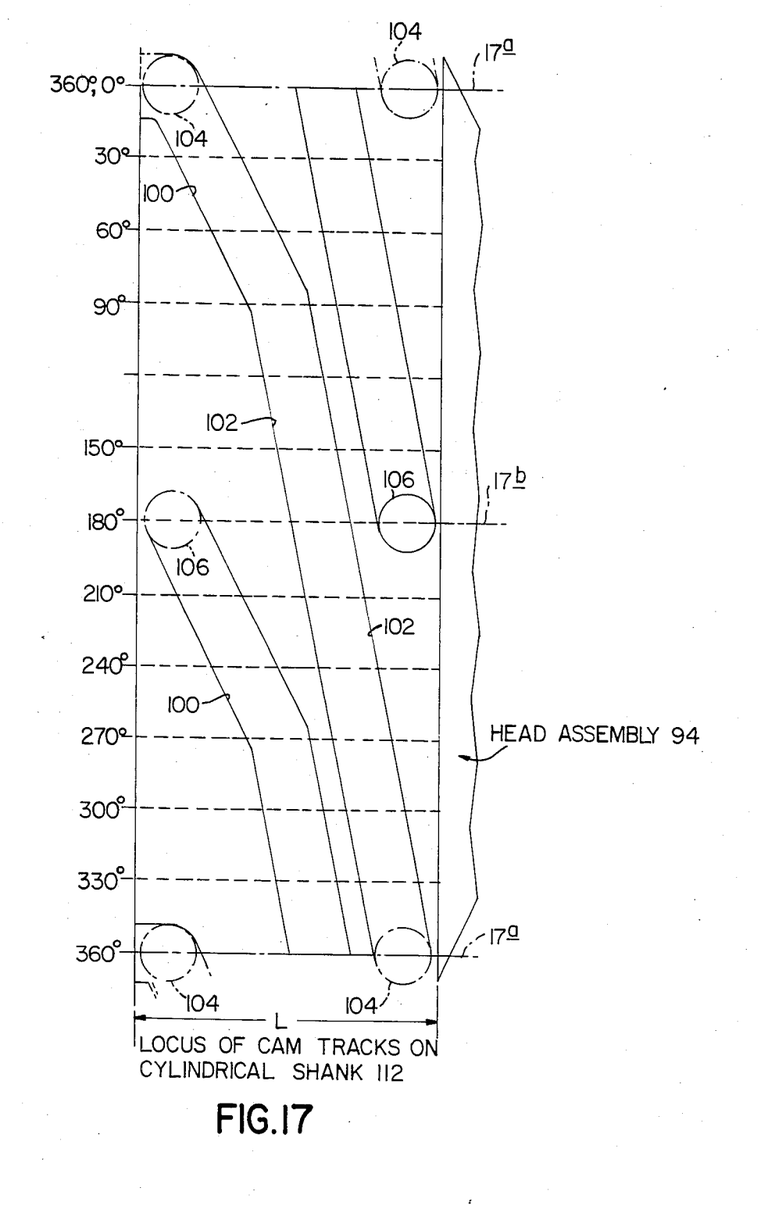
FIG. 17 is a development of the cam slot arrangement for the holder embodiment shown in FIGS. 11–16, taken on the line 17, 17 of FIG. 15.

The head assembly 32 is a two-piece arrangement wherein the stop ring 38 is press fitted in a bore 46 in the outer axial end of the shank 36. The stop ring, as best illustrated in FIG. 9, is of stepped configuration having a circumferentially extending bead 50 which seats against the axial end face 52 of the shank 36. The stop ring also has a circumferentially extending, internally radially inwardly directed bead 54 of a predetermined diameter to frictionally engage the push rod tip 56 and normally support it in a retracted position nested in the head assembly which facilitates assembly of the cartridge without interference from the plunger rod. Thus, the diameter D of the internal bead 54 of the stop ring is preferably smaller than the maximum diameter $D_1$ of the push rod tip 56 to facilitate this temporary positioning and gripping action. The plunger rod may be held in a retracted position by other means. For example, the plunger rod may be enlarged adjacent the tip portion to provide a slight interference fit in the bore of the shank when the plunger is moved to a fully retracted position. By this arrangement, when the plunger is advanced so that the enlarged portion of the plunger rod is disposed outside the shank bore, the plunger rod slides freely in the shank bore by reason of the normal clearance therebetween.

Other features of the holder of the present invention comprise a predetermined thread configuration between the shank and the collar portion which combine with the different materials between the two parts to produce quick actuation to seat the cartridge and a firm locking engagement between the head assembly and which produces a firm locking of the plunger under axial load without slippage or overhauling. The complementary threads 60, 62 of the shank 36 and collar 30 respectively are preferably a multi-start thread configuration and at least a three start thread configuration. For example, the thread specification may be as follows:

⅜ UNF, 3 A modified thread
0.200 lead, 0.04 pitch
5 start thread
Pitch diameter 0.3461–0.3490
Major diameter 0.375

Consider now assembly and use of a cartridge in a holder made in accordance with the present invention. With the head assembly in a fully retracted position and with the plunger fully retracted, the parts are in position to receive a cartridge C. Note that the plunger rod stays in a retracted position when manipulating the assembly to seat a cartridge therein by reason of the frictional engagement of the plunger rod tip in the stop ring. This eliminates one moving part from interference in the assembly process. The needle end of a cartridge is then passed through the discharge opening with the cartridge slightly tilted. Note the entry ramp allows easy insertion of the cartridge during this phase of the assembly process. With the cartridge fully in place, and the assembly supported in one hand of the user, the user simply rotates the head assembly with the other hand until the stop ring abuts the end of the cartridge and firmly supports it in place. The plunger rod is then pushed inwardly and rotated to secure it to the threaded stud of the plunger and ready the syringe for use. After the cartridge is spent, the plunger is disassembled from the plunger and the head assembly retracted and the spent cartridge is easily removed from the open end of the housing.

As noted above, the fast-action and locking effect between the head assembly and collar is enhanced by making these two parts of two dissimilar materials. The whole housing 21 is most preferably made from a clear material so as to permit maximum visibility during loading, use and removal of the cartridges. The housing 21, in addition to being sufficiently transparent, must be impact resistant, easy and inexpensive to form and to machine, and must be compatible with all of the medical and hospital environments in which it is intended to be used. Preferred materials for the housing will comprise tough, machinable, heat resistant, transparent materials. Among these preferred materials are various thermoplastics which can be injection molded into the desired part configuration with or without machining to accurately define dimensions, shapes and tolerances.

Some of the polystyrene resins, for example, can be formed into housings which are clear, strong, resistant and machinable. Various families on the polycarbonate thermoplastic resins are also highly suitable materials for use in housings in accordance with this invention. One particular thermoplastic resin which is admirably suited for use as a material for the housing means of this invention is a polyphthalate carbonate copolymer manufactured by General Electric Company and sold under the trademark LEXAN®. Specifically, LEXAN®PPC 4501 polyphthalate carbonate copolymer resin is a preferred material for use as a material for the housing of the present invention. LEXAN®PPC 4501 is clear, heat and moisture resistant, hard and strong, and can be made with desired tolerances after being injection molded or otherwise formed into a desired shape. The resulting formed housing is hard and relatively smooth, having a coefficient of friction which is relatively low.

While the entire housing 21 is described as being hard, clear and resistant to environmental degradation, the collar 30 should also have a relatively low coefficient of friction. A low coefficient of friction allows the threads 62 of the collar 30 to cooperatively operate with the shank as hereinafter described in greater detail, so that the relative movement between the complementary threads 60 and 62 permits ease of relative motion when there is no axial load applied and also provide excellent retaining forces when an axial load is present. Accordingly, the material from which the collar is formed should have a relatively low coefficient of friction. Again, all of the materials described above as being suitable for the housing 21 are, of course, suitable for the collar 30 and the threads 62.

As has been stated, the threads 62 of collar 30 cooperate with the threads 60 of the shank 36. In order to achieve the cooperative functioning of the two parts, it is necessary that the collar 30 and shank 36, or at the very least the threads 62 and 60, be made from dissimilar materials. One of the materials, either for the shank or the housing, should be somewhat softer or more rubber-like and should have a higher coefficient of friction. When one part is harder and has a lower coefficient of friction with respect to the other, it has been found that there is, surprisingly, an ease of relative motion when there is no axial load applied and yet there is, again surprisingly, excellent retaining forces when an axial load is present. Since the two parts have relatively different hardness, there is no tendency or at least a substantially reduced tendency to form microwelds between the two contacting surfaces. Since the two parts have relatively different coefficients, there is ease of movement under no load and retaining forces when an axial load is present.

Because of the desire that the housing be hard and clear, for the reasons described above, it is preferred that the shank member 36 be formed from a softer material having a higher coefficient of friction. While many materials are suitable, it is preferred that the shank 36 be formed from thermoplastic materials which can be molded to a desired shape, machined or otherwise precision-shaped such as where the threads 60 are formed. Elastomeric resins which are relatively hard as elastomers and yet not as hard as materials from which the housing is formed, can be used to manufacture the shank of this invention Acrylonitrile butadiene styrene resins which have high gloss and median impact resistance are preferred choices for the shank material. A preferred material is an ABS resin manufactured by Monsanto Company under the trademark LUSTRAN®ABS 248 resin. Other materials having similar hardness and coefficient of friction properties are also suitable for this material.

It is, of course, possible to select materials in which the shank portion 36 is both harder and smoother than the housing 30. Because of the requirement that the housing be clear and resistant to impact, however, it is more practical to select a softer, higher coefficient of friction material for the shank, and, in fact, the entire head assembly.

In either case, however, the relative relationship between the two parts 30 and 36, at least at the threads 62 and 60, should be such that there is a difference in hardness between them. Preferably, hardness differences should measure on the Rockwell R Scale of hardness of at least 5 and preferably from 8 to 30. Differences in hardness on the Rockwell R Scale of more than 30 are not as desirable. In one successful embodiment of this invention, the housing 21, including the collar 30 and threads 62 are formed from the previously referenced polyphthalate carbonated copolymer LEXAN®PPC 4501, which has a Rockwell R Scale hardness typically of 122. The shank 36 and thread 60 were formed from an ABS resin, LUSTRAN®ABS 248 resin, which had a Rockwell R Scale hardness typically of 112. Thus, the collar 30 is harder than the shank 36, as measured by Rockwell R Scale by 10 units on that scale. This is a preferred combination of dissimilar materials.

Similarly, the relative relationship between these same parts in their relative coefficient of friction properties also requires that there be a difference. Actual measurement of the coefficient of friction for molded parts and particularly for threads such as threads 60 and 62 is difficult and imprecise at best. Accordingly, the best way presently known to specify the relative relationship of the two surfaces and their respective coefficient of friction is that there, in fact, be a difference in coefficient of friction. Preferably the difference will be at least 0.1. Most preferred are materials where the difference in coefficient of friction between them ranges from 0.2 to 0.4.

The configuration and arrangement of the holder of the present invention provides certain functional advantages over the prior art. For example, with the particular thread configuration, the shank can be made comparatively long to thereby accommodate cartridges of various axial lengths without sacrificing speed of assembly. For example the head assembly can be fully seated over its maximum range with ease and with about only one and one-half turns. Further, the particular seating and nesting arrangement of the plunger rod tip facilitates assembly of cartridges without interference. In accordance with the configuration described, the shank and collar threads are always interengaged thereby ensuring good alignment at all times and this arrangement eliminates the possibility of cocking or jamming which is characteristic of some prior assemblies. Moreover, the use of the device to assemble the plunger is obvious to the user as compared with prior systems which utilize a separate screw element in the head assembly. Moreover, the transparent housing provides full visibility of the cartridge in any relative position of the head assembly and housing so that the user can observe blood flashback, air entrapment, particulate matter and other incompatibilities. In other words, at every relative angular position of the head and housing, there is always good visibility of the cartridge.

There is illustrated in FIGS. 13–20 another embodiment of holder assembly in accordance with the present invention. The holder, as illustrated, comprises an elongated housing 80 of generally U-shaped cross section having a longitudinally extending slotted opening 82 for inserting a cartridge C. At its outer terminal end, the housing has an end wall 84 with an opening 86 having a slanted discharge ramp 88 through which the needle 90 and hub portion 92 of the cartridge engage. In the present instance, means is provided connecting the head assembly 94 to the housing 80 to facilitate quick actuation of the head assembly between opposite limit positions during assembly and disassembly of a cartridge C. The means also provides automatic locking means when the head assembly has been rotated to a predetermined position exerting an axial load on a cartridge C mounted in the holder. This means comprises in the present instance, a series of cam slots 100, 102 and cam followers 104, 106 in the form of detents on the inner end of the housing which engage in the cam slots. The slot are of a preselected differing pitch to provide a quick advance during the initial actuation from a retracted position to seat the cartridge and then a more gentle slope in the latter stages of the seating process to provide a good locking action when an axial force is present to seat the cartridge in place in the housing. For example, the entrance cam slot 100 may be at an angle of about 25° to the axis of the shank and the locking cam slot portion 102 may be at an angle of about 10° to the axis of the shank. Similar to the previously described embodiment, the plunger rod 110 extends through the shank portion 112 of the head assembly and is frictionally retained therein and is normally disposed in a fully retracted position by friction engagement in the bore thereof.

The housing is also transparent to permit the user to read the dosage levels or recheck the medication and this is an advantage over prior art assemblies. Field studies have also shown that the users noted the reduction of steps from loading to locking as approximately one turn or less as providing an easy, convenient and time-saving assembly.

While a particular embodiment of the invention has been illustrated and described herein, it is not intended to limit the invention and changes and modifications may be made therein within the scope of the following claims. For example, the locking effect between the head assembly and shank may be enhanced by deliberately roughening the interfacing surfaces of the interengaging threads.

What is claimed is:

1. A holder for cartridges or containers for medicaments in injectable form comprising an elongated housing having a pocket for the cartridge, a head assembly including an elongated plunger rod adapted to be attached to the cartridge plunger for actuating the same to effect discharge of medicament from the cartridge, means operatively connecting the head assembly to one end of the housing for actuating a shank portion of the head assembly axially in the housing, said head assembly and housing having complementary threads having confronting thread surfaces and each surface having a different coefficient of friction to facilitate relative rotation of the head assembly and housing and resist slippage when the shank exerts an axial force on the cartridge to seat it in the housing.

2. The device of claim 1, wherein said head assembly and said housing are made from different materials whereby the hardness of one material with respect to the other is at least 5 units higher on the Rockwell R Scale hardness test.

3. The device of claim 2, wherein said housing is made from the harder material.

4. The device of claim 3, wherein the difference in Rockwell R Scale hardness is from about 10 to about 20 units.

5. The device of claim 4, wherein said head assembly and said housing are made from different materials whereby the coefficient of friction of one material with respect to the other is at least 0.1.

6. The device of claim 5, wherein said housing has the lower coefficient of friction.

7. The device of claim 6, wherein the difference in coefficient of friction is from about 0.2 to about 0.4.

8. The device of claim 4, wherein said head assembly is made from an ABS resin and the housing is made from a polyphthalate carbonate copolymer resin.

9. The device of claim 7, wherein said head assembly is made from an ABS resin and the housing is made from a polyphthalate carbonate copolymer resin.

10. A holder for cartridges or containers for medicaments in injectable form comprising an elongated housing having a pocket for the cartridge, a head assembly including an elongated plunger rod adapted to be attached to the cartridge plunger for actuating the same to effect discharge of medicament from the cartridge, means operatively connecting the head assembly to one end of the housing for actuating a shank portion of the head assembly axially in the housing between a retracted and extended position, said head assembly and housing being made of dissimilar materials to facilitate relative rotation of the head assembly and housing and resist slippage when the shank exerts an axial force on the cartridge to seat it in the housing, and means for detachably locking the plunger rod in a retracted position.

11. A holder as claimed in claim 10, wherein the bead assembly includes a stop ring and wherein the internal diameter of a bead of the stop ring is smaller than maximum diameter of the push rod tip.

12. A holder for cartridges or containers for medicaments in injectable form comprising an elongated housing having a pocket for the cartridge, a head assembly including an elongated plunger rod adapted to be attached to the cartridge plunger for actuating the same to effect discharge of medicament from the cartridge, means operatively connecting the head assembly to one end of the housing for actuating a shank portion of the head assembly axially in the housing, said means comprising a series of cam slots and detents on the inner side of the housing engageable in the cam slots, said slots being of a predetermined differing pitch to provide a quick advance during initial actuation from a retracted position and a more gentle slope to provide secure locking action, said head assembly and housing being made of dissimilar materials to facilitate relative rotation of the head assembly and housing and resist slippage when the shank exerts an axial force on the cartridge to seat it in the housing.

13. A holder for cartridges as claimed in claim 10, wherein said housing is made of a clear plastic material.

14. A holder for cartridges as claimed in claim 10, wherein said head assembly is of a t-shaped cross section including a pair of transversely extending wings for actuating the threaded shank portion to lock a cartridge in place and also for use in discharging contents of the cartridge.

* * * * *

UNITED STATES PATENT AND TRADEMARK OFFICE
CERTIFICATE OF CORRECTION

PATENT NO. : 4,744,790

DATED : May 17, 1988

INVENTOR(S) : Jankowski et al

It is certified that error appears in the above-identified patent and that said Letters Patent is hereby corrected as shown below:

Claim 5, line 1; change the numeral "4" to --1--

Signed and Sealed this

Fourteenth Day of March, 1989

Attest:

DONALD J. QUIGG

*Attesting Officer*     *Commissioner of Patents and Trademarks*